(12) United States Patent
Bruder et al.

(10) Patent No.: US 7,184,513 B2
(45) Date of Patent: Feb. 27, 2007

(54) METHOD FOR PRODUCING CT IMAGES OF AN EXAMINATION OBJECT HAVING A PERIODICALLY MOVING SUBREGION

(75) Inventors: Herbert Bruder, Hoechstadt (DE); Thomas Flohr, Uehlfeld (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 236 days.

(21) Appl. No.: 11/019,630

(22) Filed: Dec. 23, 2004

(65) Prior Publication Data

US 2005/0195937 A1    Sep. 8, 2005

(30) Foreign Application Priority Data

Dec. 23, 2003    (DE)    ............................ 103 60 981

(51) Int. Cl.
*A61B 6/03*    (2006.01)
(52) U.S. Cl. .......................................... 378/8; 378/901
(58) Field of Classification Search .............. 378/1–21, 378/210, 901; 382/130–132, 262; 600/428
See application file for complete search history.

(56) References Cited

U.S. PATENT DOCUMENTS

| | | | |
|---|---|---|---|
| 6,041,132 A * | 3/2000 | Isaacs et al. ................. | 382/100 |
| 6,047,039 A | 4/2000 | Flohr ............................. | 378/4 |
| 6,434,215 B1 * | 8/2002 | Cesmeli ......................... | 378/8 |
| 6,466,640 B1 | 10/2002 | Taguchi ........................ | 378/15 |

OTHER PUBLICATIONS

CT Angiography: In Vitro Comparison of Five Reconstruction Methods, Addis et al., Nov. 2001, American Roentgen Ray Society.*
Willi A. Kalender, "Computer-tomographie", ISBN 3-89578-082-0, Chapter 6, pp. 146-157.

* cited by examiner

*Primary Examiner*—Courtney Thomas
*Assistant Examiner*—Alexander Taningco
(74) *Attorney, Agent, or Firm*—Harness, Dickey & Pierce, P.L.C.

(57) ABSTRACT

A method and a CT unit are proposed for producing CT images of an examination object having a periodically moving subregion, preferably a beating heart, by multiplanar reconstruction. Subsequent to joining the axial images with pixels from a number of partial volumes calculated for the rest phases, a reduction takes place to reduce artifacts occurring in overlap regions. This is done by carrying out threshold value formation in the zone of the boundary regions of the partial volumes with result image $D_z$. A pixel-oriented median filtering then occurs, resulting in image $M_z$. A differential value image is then produced using $F_z = D_z - M_z$. Subsequently, two-dimensional lowpass filtering is applied to $F_z$ to produce a result image $G_z$. Finally, a calculation of $B_z - G_z$ is used to form the final image $E_z$.

20 Claims, 3 Drawing Sheets

METHOD FOR PRODUCING CT IMAGES OF AN EXAMINATION OBJECT HAVING A PERIODICALLY MOVING SUBREGION

The present application hereby claims priority under 35 U.S.C. §119 on German patent application number DE 103 60 981.4 filed Dec. 23, 2003, the entire contents of which are hereby incorporated herein by reference.

FIELD OF THE INVENTION

The invention generally relates to a method for producing CT images of an examination object having a periodically moving subregion, preferably a beating heart. In such a method, the examination object may be scanned with the aid of at least one detector by at least one preferably spiral-shaped focus that is moved around this object and forms a radiation beam. At the same time, movement information of the moving subregion may be detected and stored and can be used to determine individual movement and/or rest phases. A multiplicity of tomograms doubly inclined to the system axis may be reconstructed, per cycle for partial volumes of the moving subregion, from the collected detector data, axial tomograms, perpendicular to the system axis, for the partial volumes being calculated from the doubly inclined tomograms, and for the purpose of reducing step artifacts in the boundary region of the partial volumes, the total examination volume of the examination object being assembled from the axially illustrated partial volumes in the specific rest phase section by interpolative mixing.

BACKGROUND OF THE INVENTION

A known method is fundamentally known as MPR (MPR=multiplanar reformating) method from Willi A. Kalender, Computertomographie, [Computer Tomography], ISBN 3-89578-082-0, chapter 6. The application of this MPR method in cardio-computer tomography is also generally known.

In order to reduce so called ring artifacts, DE 198 35 451 A1 describes a method for post-processing of a reconstructed CT tomogram that, however, is applied to CT images of stationary objects and operates in the axial image layers. This line balancing method outlined there and including median filtering, threshold value formation, differential image production and subsequent angle smoothing is not, however, suitable for the cardio CT method. It is conceived only for transverse tomograms, where line artifacts are eliminated.

The problem additionally arises with an MPR cardio CT that the assembly of the total examination volume from partial volumes that have been measured over a number of cardiac cycles gives rise at the transition regions of the partial volumes to an increased number of step artifacts that then need additionally to be reduced.

SUMMARY OF THE INVENTION

It is therefore an object of an embodiment of the invention to find a method for producing CT images of a examination object having a periodically moving subregion, preferably a beating heart. Preferably, the method reduces or, if possible, completely removes step artifacts that occur and which are produced when the total recording volume is assembled from a number of partial volumes.

A method is proposed for producing CT images of an examination object having a periodically moving subregion, preferably a beating heart, in which:

the examination object is scanned with the aid of at least one detector by at least one preferably spiral-shaped focus that is moved around this object and forms a radiation beam, at the same time movement information of the moving subregion is detected and stored and can be used to determine individual movement and/or rest phases, axial tomograms $B_z(x, y)$ are calculated from the collected detector data of the rest phases, and the total examination volume of the examination object is assembled in the specific rest phase section from the axially illustrated partial volumes by interpolative mixing, as a result of which step artifacts in the boundary region of the partial volumes are reduced, wherein after the assembly of the total examination volume, consisting of a multiplicity of axial original images $B_z$ with pixel values $B_z(x,y)$, in the zone of the boundary regions of the partial volumes the CT values are limited in at least one image plane z to a prescribed value range with an upper and a lower bound ($\Delta_1 \leq D_z(x,y) \leq \Delta_2$), thus producing a result image $D_z$, a pixel-oriented median filtering is carried out on the result image $D_z$, thus producing a result image $M_z$, a differential value image $F_z$ is calculated from the result images $D_z$ and $M_z$ using $F_z=D_z-M_z$, a two-dimensional lowpass filtering is applied to the error image $F_z$, thus producing a result image $G_z$, and the result image $G_z$ is subsequently subtracted from the original image $B_z$ and a final image $E_z$ is obtained.

This method may largely suppress the step artifacts otherwise existing at the boundaries of the partial volumes that are produced by the assembly of the partial volumes.

It is to be noted here that the illustrated method can be applied in general to step artifacts at boundary layers of assembled partial volumes which occur in the case of cardio reconstruction methods with and without cone-beam correction and/or with and without axial reformatting steps. In a preferred design—corresponding to a calculation of the tomograms with cone correction—the original tomograms can be calculated, for example, by reconstructing, per cycle for partial volumes of the moving subregion, a multiplicity of tomograms doubly inclined to the system axis from the collected detector data, and subsequently calculating from the doubly inclined tomograms, axial tomograms, perpendicular to the system axis, for the partial volumes, which then form the original tomograms $B_z$.

The method can optionally be expanded to the effect that a threshold value limitation with an upper and a lower bound ($\Delta'_1 \leq F_z(x,y) \leq \Delta'_2$) is applied to the error image $F_z$, thus producing an error image $F'_z$ that replaces the error image $F_z$ in the further calculation method.

In a further preferred variant of the method, the pixel-oriented median filtering is carried out on the result image $D_z$ in an orthogonal direction relative to the axial image plane, although it is also possible for small deviations from the orthogonal direction to be tolerated and to lie within the scope of the embodiments of the invention.

In a preferred further development of the method, it is proposed to determine the boundary regions of the partial volumes on the basis of the frequency of the movement cycle, preferably the heart rate, and the rate of rotation of the focus, and thereby to identify the regions to be subjected to compensation calculation. This can be done, for example, using the following formula:

$$z_1 = z_0 + \frac{T_r + T_{Rev}}{T_{rot}} \cdot v \text{ and}$$

$$\Delta z = v \cdot \frac{T_H}{T_{rot}}$$

where:

$z_0$=starting position of the scan;
$z_1$=start of the partial volume;
$T_H$=heart cycle frequency;
$T_R$=time to last R peak in ECG;
$T_{rot}$=rotation time;
$T_{rev}$=time delay with reference to this last R peak;
v=feed.

Furthermore, in a preferred way the pixel-oriented median filtering for the result image $M_z$ can be carried out orthogonally relative to the boundary between the partial volumes of the respectively considered region. Here, as well, small deviations from the orthogonal direction can be tolerated and are within the scope of the embodiments of the invention.

If the aim is to render the described algorithm effective only in a region of soft parts, for threshold value formation in the MPR layer, the prescribed value range of the CT values can be set at 1000HU +/−Δ, it being necessary to adapt the magnitude of Δ in accordance with the results achieved thereby.

It is also advantageous when the length of the median filter corresponds at least to the interpolation length used at the stack boundaries (=boundaries of the partial volumes), and the interpolated image layers at the sack boundary are preferably not incorporated in the median calculation.

Sliding averaging can be used as low pass filtering.

In addition a computer tomography unit is proposed for producing CT images of an examination object having a periodically moving subregion, preferably a beating heart, comprising:

a focus that scans the examination object, on a spiral track with the aid of a radiation beam and a detector, a means for acquiring and storing movement information, preferably an ECG with evaluation unit, with the aid of which individual movement and/or rest phases can be determined, a control and evaluation unit for controlling at least one drive unit of the focus and, if appropriate, of the at least one detector, including collecting and storing the detector and movement data, in which means are provided which during operation use the collected detector data of the rest phases to calculate axial tomograms $B_z$(=original images) with pixels $B_z(x,y)$, and use the axially illustrated partial volumes to assemble the total examination volume of the examination object in the specific rest phase section by interpolative mixing, to the effect that a threshold value device for limiting the CT values in the zone of the boundary regions of the partial volumes in at least one image plane z to a prescribed value range with an upper and a lower bound ($\Delta_1 \leq D_z(x,y) \leq \Delta_2$) which is provided outputs result images $D_z$, a median filter is provided that carries out a pixel-oriented median filtering on the result image $D_z$, thus producing a result image $M_z$, a differential image device is provided that calculates a differential value image $F_z$ from the result images $D_z$ and $M_z$ using $F_z=D_z-M_z$, a lowpass filter is provided that imposes a two-dimensional lowpass filtering over the error image $F_z$ and outputs a result image $G_z$, and a further differential image device is provided that subtracts the result image $G_z$ from the original image $B_z$, and outputs a final image $E_z$.

Furthermore, a computer tomography unit is also proposed including means, preferably program means, that during operation carry out the further previously described method steps.

BRIEF DESCRIPTION OF THE DRAWINGS

The invention is described in more detail below with reference to a preferred exemplary embodiment and with the aid of the figures, the following reference numerals being used: 1 computer tomography unit; 2 x-ray tube; 3 detector; 4 opening; 5 housing; 6 patient couch; 7 system axis/z-axis; 8 control/evaluation unit with ECG; 9 ECG line; 10 retrospective recourse; 11 R wave; 12 partial volume; 13 overlap region of the partial volumes; 14 total volume; 15 time profile of the z-position of the detector rows; P patient; $Prg_n$ program/program modules; α angle of rotation; I-X method steps.

In particular.

DETAILED DESCRIPTION OF THE EXEMPLARY EMBODIMENTS

Figure 1:
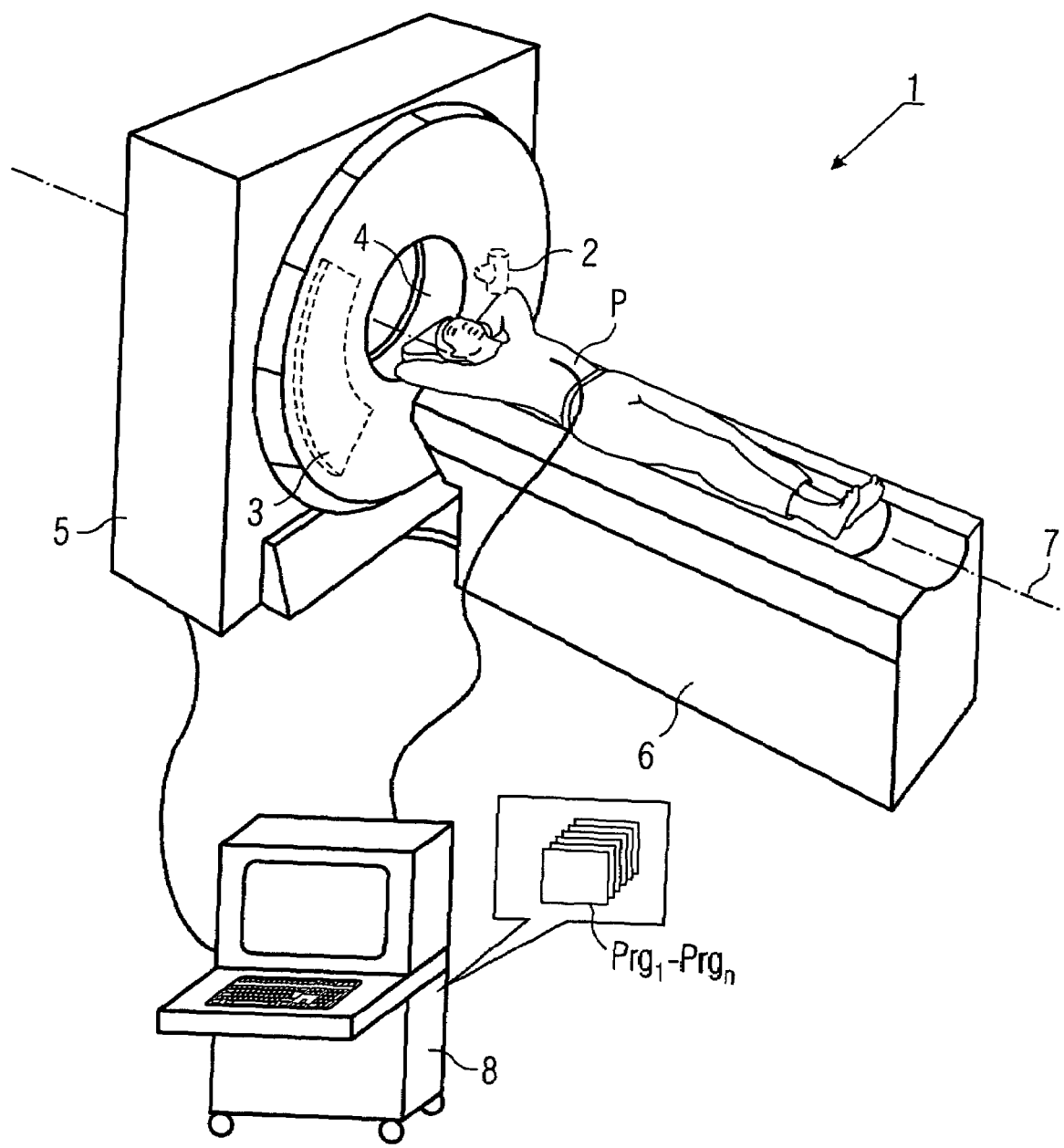
FIG. 1 shows a schematic of a CT unit for producing a cardio CT.

FIG. 1 shows a three-dimensional schematic of a preferred exemplary embodiment of a cardio computer tomography unit 1 having an x-ray tube 2 and an oppositely situated detector 3 that are fitted on a gantry—not illustrated—in a fashion capable of rotation inside the housing 5. The actual focus, from which the conical radiation beam scanning the patient P emerges, is situated—not visibly—inside the x-ray tube. In a fashion controlled by the control and evaluation unit 8 and the control and evaluation programs $Prg_n$ integrated therein, the patient P is moved along the z-axis 7 with the aid of the movable patient couch 6 through the opening 4 of the computer tomography unit 1, while at the same time the gantry rotates with the focus and detector about the z-axis 7. A spiral movement track of the focus, referred to the movement system of the patient, results in this way.

At the same time as the patient P is being scanned by x-rays, the movement signals of the heart are scanned via an ECG integrated in the control/evaluation unit 8, it being possible for the temporarily present rest phase to be determined mostly retrospectively with reference to the respectively measured cardiac cycle and with the aid of the R wave detected in the ECG.

Figure 2:
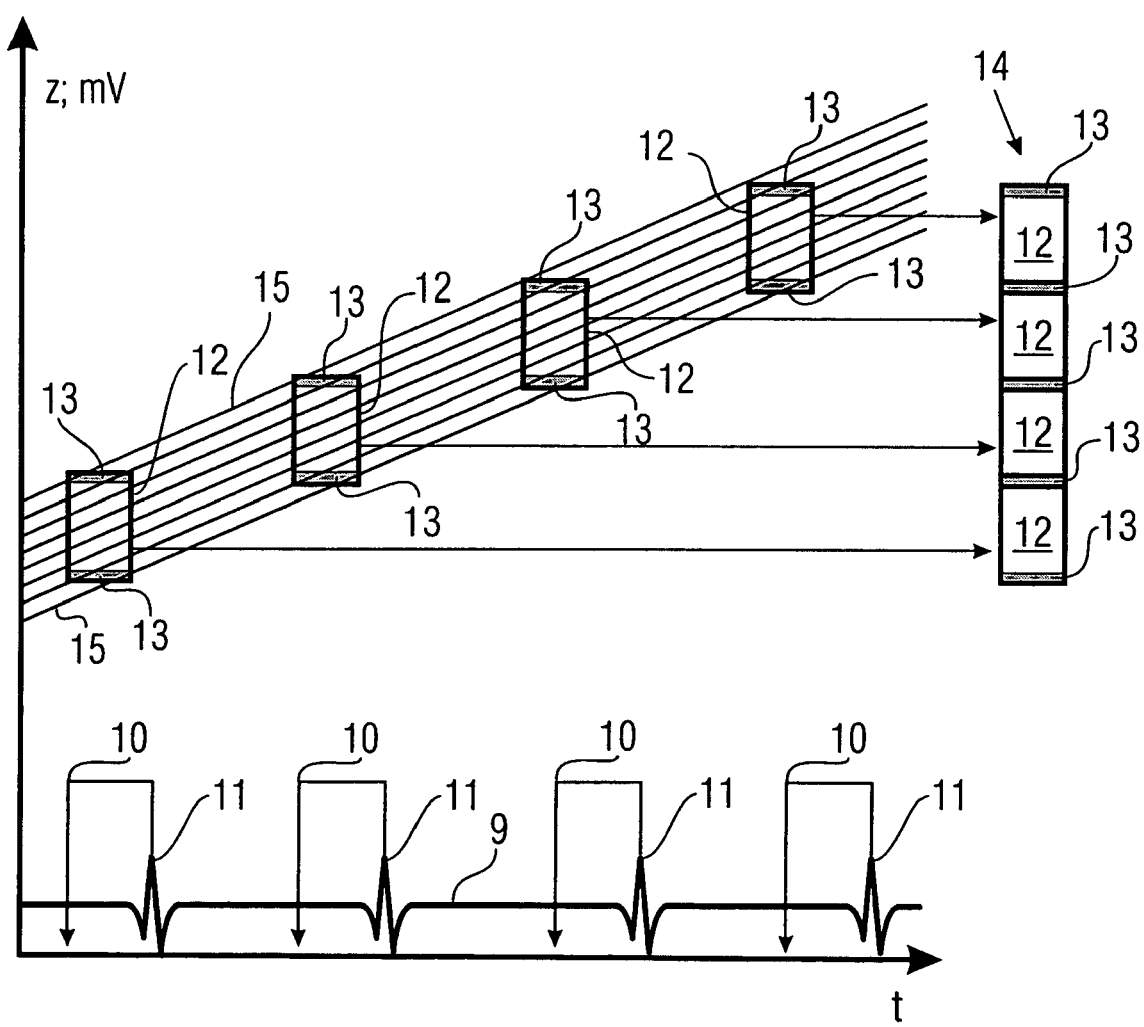
FIG. 2 shows a schematic of the data acquisition from rest phases of the heart.

The production of the tomographs of the total examination volume with utilization of the rest phases of the heart is illustrated in FIG. 2. In the lower part of a coordinate system, this figure shows the ECG line 9, recorded parallel to the scan, with four R-waves 11 that are plotted along the time axis t. The electric cardiac muscle potential measured via the EGC is plotted in mV on the ordinate. The backwardly directed arrows 10 represent the retrospective determination of the start of the rest phase, which simultaneously reproduces the start of the useful CT data.

The schematic time profile of a multi-row CT detector is plotted above the ECG illustration along the system axis of the CT unit. In a fashion corresponding to this, the angle of rotation β, which varies in direct proportion to time on the basis of the constant spiral course is plotted on the abscissa. The ordinate shows the z-position on the system axis. The continuously rising lines 15 are intended to illustrate the z-position of the individual detector rows. Illustrated in accordance with the respective start of a rest phase are the regions 12 which represent the data collection of the scan over the rest phase and also the partial volumes scanned in the rest phase with the tomograms reconstructed there. Positioned below in grey in these partial volumes 12 are overlap regions 13 in which two-fold tomograms from neighboring partial volumes 12 are present.

In order to illustrate the entire examination volume, the partial volumes 12 scanned in the rest phases are combined in a way known per se to form a total volume 14, the partial volumes being joined by interpolative mixing. Thus, partial volumes are combined to form total volumes by applying interpolation and mixing algorithms. The aim of this is to reduce step artifacts in the overlap regions. However, if this is not sufficiently successful, the method, or even the previously known method, may be applied once more to this total volume 14.

Figure 3:
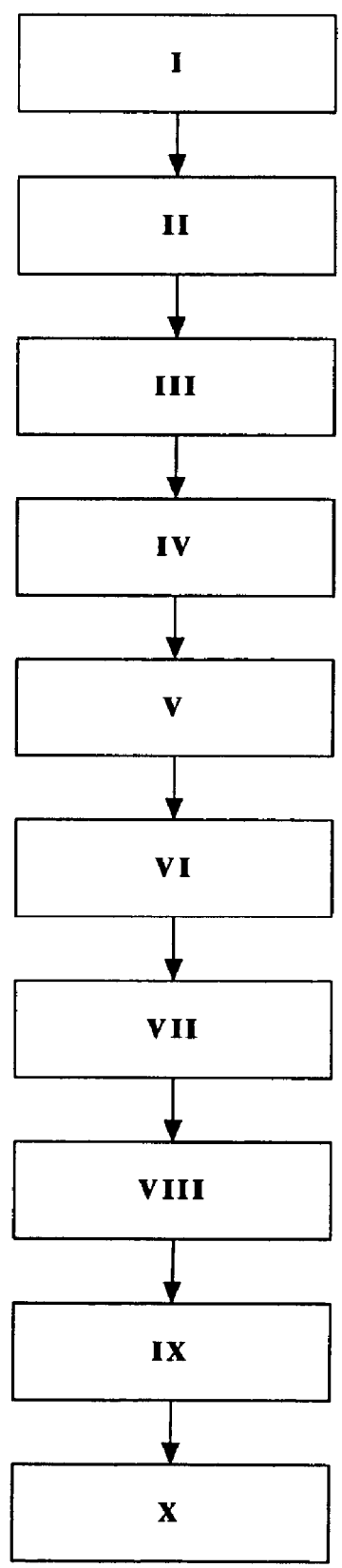
FIG. 3 shows a flowchart of the method according to an embodiment of the invention.

FIG. 3 shows these method steps according to an embodiment of the invention in a brief summary. The individual method steps are named using Roman numerals. In detail:

I. signifies scanning of the examination object;
II. signifies parallel ECG recording of the heart;
III. signifies calculation of axial tomograms $B_z$ of the partial volumes;
IV. signifies interpolative mixing of the partial volumes to form a total volume;
V. signifies forming the threshold value in the zone of the boundary regions of the partial volumes ($\Delta_1 \leq D_z(x,y) \leq \Delta_2$) with result image $D_z$;
VI. signifies pixel-oriented median filtering with result image $M_z$;
VII. signifies calculating differential value image $F_z = D_z - M_z$;
VIII. signifies that a threshold value formation can now optionally be applied to $F_z$, with ($\Delta'_1 \leq F_z(x,y) \leq \Delta'_2$) to form the error image $F'_z$, which in this case replaces the error image $F_z$;
IX. signifies two-dimensional lowpass filtering on $F_z$ or optionally the result $F'_z$ with result image $G_z$; and
X. signifies calculation of $B_z - G_z$ = final image $E_z$.

If the axial tomographs of the total volume are treated computationally in accordance with this method, there is a consequent significant reduction in any step artifacts possibly present in the boundary region of the partial volumes, the result thus being an improved imaging for diagnostics of the heart.

It is to be pointed out that the method outlined can be applied not only for spiral CT recordings, but also in the sequential recording technique. In this sequential recording technique, the scanning is done with the couch feed suspended, and the x-ray tube is switched off as the couch is being fed to the next z position. Thus, the couch is fed sequentially, and not continuously as in the case of spiral CT. Here, the position of the partial volumes can be determined solely from the step-wise couch feed and the orientation of the multi-planar reconstruction.

It goes without saying that the above-named features of an embodiment of the invention can be used not only in the combination respectively specified, but also in other combinations or on their own without departing from the scope of the invention.

Thus in summary, an embodiment of the invention specifies a method and a CT unit for producing CT images of an examination object having a periodically moving subregion, preferably a beating heart, by multiplanar reconstruction, in which subsequent to joining the axial images $B_z$ with pixels $B_z(x,y)$ from a number of partial volumes calculated for the rest phases, a reduction takes place in the step artifacts occurring in overlap regions by carrying out threshold value formation in the zone of the boundary regions of the partial volumes ($\Delta_1 \leq D_z(x,y) \leq \Delta_2$) with result image $D_z$, a pixel-oriented median filtering with result image $M_z$, a differential value image using $F_z = D_z - M_z$, subsequently two-dimensional lowpass filtering applied to $F_z$ with result image $G_z$, and finally calculation of $B_z - G_z$ to form the final image $E_z$.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable involatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable involatile memory, such as memory cards; and media with a built-in ROM, such as ROM cassettes.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing CT images of an examination object having a periodically moving subregion, comprising:
    scanning the examination object with the aid of at least one detector;
    detecting and storing scanned data regarding the moving subregion, usable for determining at least one rest phase;
    calculating axial tomograms from the detected and stored detector data of at least one rest phase; and
    assembling, by interpolative mixing, a total examination volume of the examination object in a rest phase section from axially calculated partial volumes so as to reduce step artifacts in a boundary region of the partial volumes;

after the assembly of the total examination volume, including a multiplicity of axial original images with pixel values in a zone of the boundary regions of the partial volumes, limiting CT values in at least one image plane z to a prescribed value range with an upper and a lower bound, thus producing a result image $D_z$;

carrying out a pixel-oriented median filtering on the result image $D_z$, thus producing a result image $M_z$;

calculating a differential value image $F_z$ calculated from the result images $D_z$ and $M_z$;

applying a two-dimensional low pass filtering to the differential value image $F_z$, thus producing a result image $G_z$; and subtracting the result image $G_z$ from the original image, and obtaining a final image $E_z$.

2. The method as claimed in claim 1, wherein a threshold value limitation with an upper and a lower bound is applied to the differential value image $F_z$, thus producing a corrected error image $F'_z$ that replaces the differential value image $F_z$.

3. The method as claimed in claim 1, wherein the pixel-oriented median filtering is carried out on the result image $D_z$ in an orthogonal direction relative to the axial image plane.

4. The method as claimed in claim 1, wherein the boundary regions of the partial volumes are determined based upon the frequency of the movement cycle.

5. The method as claimed in claim 1, wherein the pixel-oriented median filtering for the result image $M_z$ is carried out orthogonally relative to the boundary between the partial volumes of the respectively considered region.

6. The method as claimed in claim 1, wherein the prescribed value range of the CT values is 1000HU +/−Δ.

7. The method as claimed in claim 1, wherein the length of the median filter corresponds at least to the interpolation length used at boundaries of the partial volumes.

8. The method as claimed in claim 1, wherein sliding averaging is used as low pass filtering.

9. A computer tomography unit for producing CT images of an examination object having a periodically moving subregion, comprising:

a focus, adapted to scan the examination object on a spiral track, with the aid of a radiation beam and a detector;

means for acquiring and storing movement information, from which at least one rest phase is determinable;

a control and evaluation unit for controlling at least one drive unit of the focus and, if appropriate, of the at least one detector, including collecting and storing the detector and movement data, the control and evaluation unit including, means for, during operation, using the detector data of rest phases per cycle for partial volumes of the moving subregion, calculating a multiplicity of axial tomograms with pixels for the partial volumes, and for using the axially illustrated partial volumes to assemble the total examination volume of the examination object in a rest phase section by interpolative mixing;

a threshold value device for limiting the CT values in the zone of the boundary regions of the partial volumes in at least one image plane z to a prescribed value range with an upper and a lower bound and for outputting a result images $D_z$;

a median filter adapted to carry out a pixel-oriented median filtering on the result image $D_z$, thus producing a result image $M_z$;

a differential image device, adapted to calculate a differential value image $F_z$ from the result images $D_z$ and $M_z$;

a lowpass filter, adapted to impose a two-dimensional lowpass filtering over the error image $F_z$ and adapted to output a result image $G_z$; and a further differential image device, adapted to subtract the result image $G_z$ from the original image $B_z$, and output a final image $E_z$.

10. A computer program, adapted to carry out the method of claim 1, when run on a computer device.

11. A method as claimed in claim 1, wherein the method is for producing CT images of a beating heart.

12. A method as claimed in claim 1, wherein the examination object is scanned with the aid of at least one detector by at least one spiral-shaped focus being moved around the object, forming a radiation beam.

13. The method as claimed in claim 2, wherein the pixel-oriented median filtering is carried out on the result image $D_z$ in an orthogonal direction relative to the axial image plane.

14. A method as claimed in claim 11, wherein the examination object is scanned with the aid of at least one detector by at least one spiral-shaped focus being moved around the object, forming a radiation beam.

15. The method as claimed in claim 14, wherein the boundary regions of the partial volumes are determined on the basis of the heart rate and the rate of rotation of the focus.

16. The method as claimed in claim 15, wherein the pixel-oriented median filtering for the result image $M_z$ is carried out orthogonally relative to the boundary between the partial volumes of the respectively considered region.

17. The method as claimed in claim 1, wherein the length of the median filter corresponds at least to the interpolation length used at boundaries of the partial volumes, and the interpolated image layers at the boundaries of the partial volumes are not incorporated in the median calculation.

18. A computer tomography unit for producing CT images of an examination object having a periodically moving subregion, for implementing the method of claim 1.

19. A computer readable medium, including the program of claim 10.

20. A method for producing CT images of an examination object having a periodically moving subregion, comprising:

scanning the examination object;

detecting scanned data of the periodically moving subregion;

calculating axial tomograms from the detected data of at least one rest phase the subregion; and reducing step artifacts in a boundary region of partial volumes, obtained from the calculated axial tomograms;

producing a result image after the assembly of a total examination volume, by limiting CT values in at least one image plane to a prescribed value range with an upper and a lower bound;

filtering on the result image to produce a second result image;

calculating a differential value image calculated from the result image and the second result image;

low pass filtering the differential value image to produce a third result image; and subtracting the third result image from the original image, to obtain a final image.

* * * * *